United States Patent [19]

Graze, Jr.

[11] Patent Number: 5,058,440

[45] Date of Patent: Oct. 22, 1991

[54] GAS SAMPLING DEVICE AND DILUTION TUNNEL USED THEREWITH

[75] Inventor: Russell R. Graze, Jr., Dunlap, Ill.

[73] Assignee: Caterpillar Inc., Peoria, Ill.

[21] Appl. No.: 577,226

[22] Filed: Sep. 4, 1990

[51] Int. Cl.$^5$ ............................................. G01N 1/00
[52] U.S. Cl. ................................................. 73/863.83
[58] Field of Search ............ 73/863.23, 863.81, 863.83,
73/864.81, 23.31, 23.32, 23.33, 28.01–28.06, 116

[56] References Cited

U.S. PATENT DOCUMENTS

| | | | |
|---|---|---|---|
| 3,699,814 | 10/1972 | Kaufman | 73/863.11 |
| 4,228,676 | 10/1980 | Myers | 73/28.04 |
| 4,361,028 | 11/1982 | Kamiya et al. | 73/23.3 |
| 4,586,367 | 5/1986 | Lewis | 73/23.33 |
| 4,660,408 | 4/1987 | Lewis | 73/28.06 |

FOREIGN PATENT DOCUMENTS 0016333  1/1982  Japan ................................ 73/863.81

OTHER PUBLICATIONS

Mott Metallurgical Corporation Brochure entitled, "Precision Porous Metal Filter Elements", publlished cira: 1989.

Sierra Instruments Brochure entitled, "Process Gas Mass Flow Controllers and Meters", published circa: 1988.

Article in Advances in Instrumentation, vol. 29, Part 3, Paper No. 708, by: Paul M. Giever, published: 1974.

*Primary Examiner*—Robert Raevis
*Attorney, Agent, or Firm*—Charles E. Lanchantin, Jr.; J. Wesley Blumenshine

[57] ABSTRACT

A gas sampling device includes a dilution tunnel of particularly effective construction that reduces contamination or soiling of the ducting leading to a filter assembly and improves the accuracy of the results. The gas sampling device has a sampling probe disposable in the gas stream of an engine or the like, and a controlled source of clean and pressurized diluent air. The dilution tunnel includes an air distribution tube defining a plurality of distribution holes therethrough, a collar defining a first annular chamber about the air distribution tube that is connected to the air source, and a porous center tube having a plurality of micron-sized pores connected between the sampling probe and the filter assembly. A second annular chamber is defined between both tubes, and the diluent air supplied thereto is uniformly passed through the porous center tube to effect good mixing of the exhaust gas and diluent air while providing a boundary layer of diluent air that keeps the center tube clean. An alternate embodiment gas sampling device employing master and slave mass flow controllers is also disclosed.

10 Claims, 2 Drawing Sheets

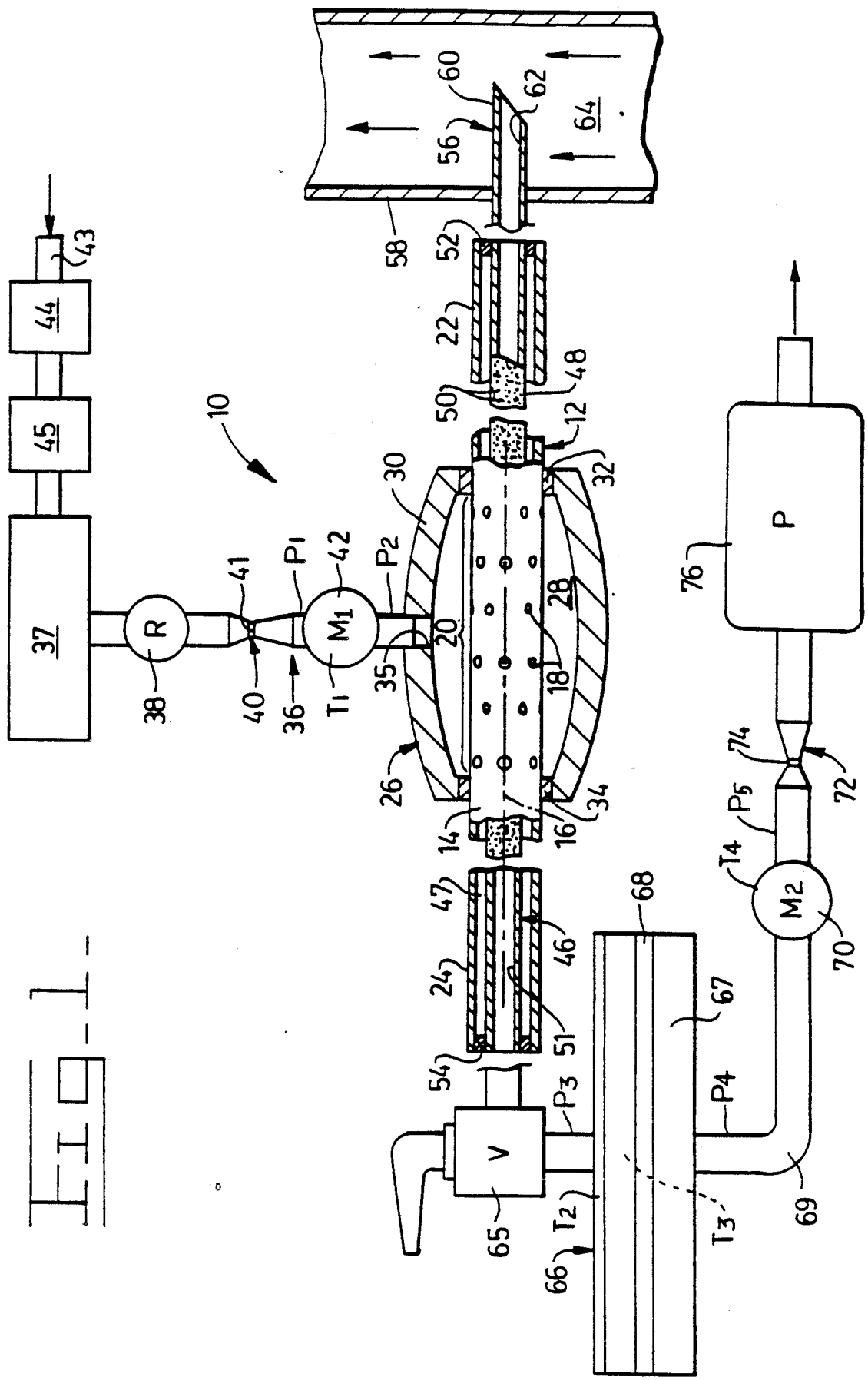
FIG_1

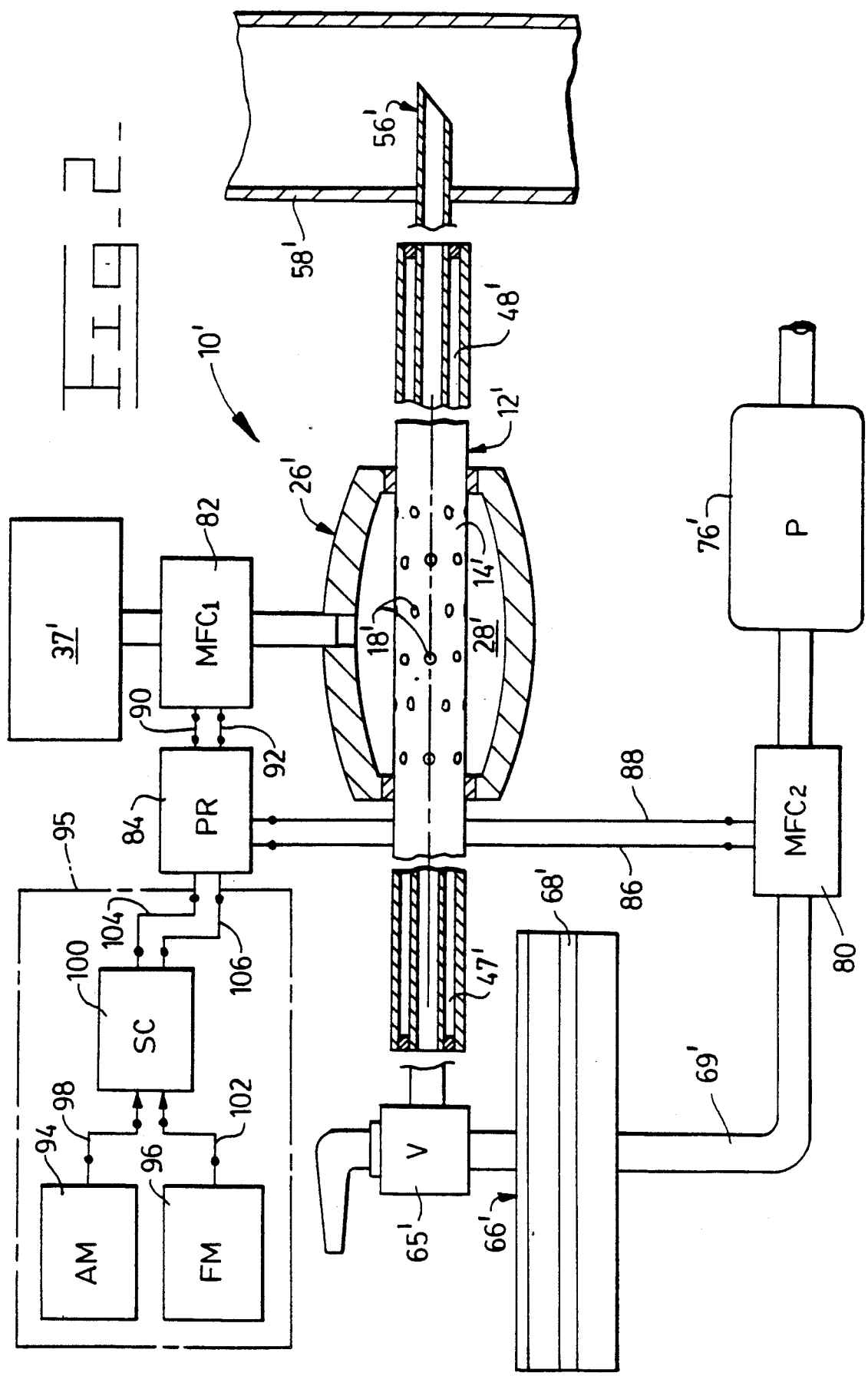

GAS SAMPLING DEVICE AND DILUTION TUNNEL USED THEREWITH

TECHNICAL FIELD

The present invention relates to a proportional sampling device for accurately measuring the amount of particulates in the exhaust gas stream of an engine or the like, and more particularly to a sampling device including a dilution tunnel for improved adiabatic cooling and mixing of the exhaust gas stream with diluent air.

BACKGROUND ART

Exhaust emissions from motorized on-highway vehicles are currently regulated by the Federal Government and must not exceed certain contaminant levels as is set forth in Title 40, Chapter I of The Code of Federal Regulations, Section 86 Subpart C. Because of these regulations increasingly more sophisticated testing equipment has been developed to test and analyze engines for conformance with such standards. For example, one recent regulation set by the Environmental Protection Agency (EPA) involves a particulate limit standard of 0.60 g/hph for diesel truck engines. These particulates are defined as matter in the exhaust gas stream, other than condensed water, which can be collected on a special filter after dilution with ambient air to a maximum temperature of 52° C.(125° F.). This includes agglomerated carbon particles, absorbed hydrocarbons, and sulphates.

U.S. Pat. Nos. 4,586,367 issued to G. W. Lewis on May 6, 1986 and 4,660,408 also issued to G. W. Lewis on Apr. 28, 1987 teach the importance of adding dilution air through a carefully controlled sampling system and introduce the philosophy of vigorously monitored secondary dilution. Sampling systems of that general class are in use in an effort to satisfy the EPA guidelines on heavy duty truck engine certification compliance. These patents also make reference to the need for eliminating errors in the measurements taken of the diluted exhaust and the diluent air streams and the need for precisely controlling these flow rates.

There has been much consideration of these dilution "tunnel" devices, and including the system of U.S. Pat. No. 4,361,028 issued to S. Kamiya et al. on Nov. 30, 1982 which teaches the relationship between filter pressure differential and accumulated filter mass. Impending legislation will extend the requirements for particulate emissions monitoring to engine sizes well beyond the practical upper limits for "full dilution" systems. The latter term referring to test arrangements wherein the total exhaust gas flow from an engine is mixed with a quantity of diluent air. For example, a locomotive engine of 4,000 Kw output emits approximately 36,000 cubic feet of 450° C. effluent each minute. To test this engine in a configuration such as is described in U.S. Pat. No. 4,586,367 would require a dilution tunnel seven feet in diameter; this is an impractical and economically unacceptable solution.

Investigations into the performance of sampling systems used today indicate excessive variability between governmental bodies, the test organizations, and the engine manufacturers. This variability exerts a negative influence. On the one hand the highlighted discrepancies between the industry test labs translate into competitive advantages for the low-result test labs. And on the other hand, the observed test-to-test variability translates into increased test expenditure because a large number of tests are required to obtain statistically significant results. Although there are several particle mechanisms that influence test-to-test variability, those most significant are particle deposition on the dilution tunnel and tailpipe walls by thermophoresis, by mechanical processes such as diffusion, gravitational sedimentation and turbulence, and by reentrainment of deposited particles and hydrocarbon gas phase exchange of the soluble portion of the diesel exhaust particulate with the deposited wall bound particulate. Therefore, elimination of the deposition mechanism is highly desirable.

The sampling systems of the aforementioned Lewis patents do not treat the phenomena of particle deposition. The long tailpipe used is not insulated nor externally heated and this creates heat transfer conditions conducive to thermophoresis. Additionally, the temperature of the fraction of the sample to obtain secondary dilution is approximately 375° F. The diluted sample is therefore subject to particle loss due to thermophoresis. The collection of material on the walls, rather than on the surface of the filter that is subsequently weighed, can throw off the test results. Furthermore, when a later test is separately run, the agglomerated material is prone to sluff off the walls and be collected by the filter. Moreover, prior systems have often been so large that significant facility support is required.

A dilution tunnel was briefly described in 1974 in an article by Paul M. Giever in "Advances In Instrumentation (Volume 29, Part 3, Paper No. 708) that included a tubular housing, and a tubular probe and a dilution air tube under it within the housing. Air passed radially outwardly from the dilution air tube into the tubular housing and radially inwardly through the probe which was made of stainless steel cloth. A laminar boundary layer of the diluent air shielded the exhaust gas sample from the probe walls while undesirably effecting very little mixing therebetween. A Reynolds number less than 2,000 was called for. Such undesirable flow conditions also restricts the degree of cooling without condensation to a lower limit of 170° F., which is not sufficient for today's standards.

In order to obtain uniformly acceptable results it is mandatory that the withdrawal of the exhaust gas sample and the addition of the diluent air be accomplished at accurately controlled flow rates. Prior gas sampling devices have incorporated relatively unsophisticated flow meters and regulators, and because of this most required continual monitoring by a test operator. In order to assure the accuracy of the test results it was necessary to take a repetitive number of temperature and pressure readings. Thereafter, the collected data had to be mathematically manipulated and correction factors applied because of the crude equipment used. Thus, the existing gas sampling devices have not been sufficiently developed for adoption by commercial industries as a standard.

Clearly, three separate needs are faced by today's diesel engine manufacturers. They are:

1. Reduction in the variability of test results in part through the elimination of thermophoretic deposition of particulates on the walls of the sampling device and corresponding hydrocarbon gaseous phase component exchange with these wall-bound particles;
2. A "down-sized", fully portable system which can yield results equivalent to laboratory systems; and
3. A sampling system that can monitor variable engine operating parameters and can automatically control the rate of exhaust gas withdrawal and can vary the air dilution rate within preselected guidelines within a normal range of operating temperatures and pressures.

The present invention is directed to overcoming one or more of the problems as set forth above.

DISCLOSURE OF THE INVENTION

In accordance with one aspect of the invention a dilution tunnel is provided for a gas sampling device including a sampling probe adapted to be disposed in an exhaust gas stream of an engine or the like, a source of clean diluent air, and a filter assembly. Advantageously, the dilution tunnel includes an air distribution tube having a plurality of distribution holes therethrough, a housing forming a first chamber about the air distribution tube, and a porous center tube having a plurality of micron-sized pores and defining a second chamber within the air distribution tube. The first chamber is connected to the diluent air source, and the center tube is connected between the sampling probe and the filter assembly.

In accordance with another aspect of the invention a gas sampling device is provided for measuring the amount of particulates in the exhaust stream of an engine or the like. The gas sampling device includes a clean air source, a filter assembly, a vacuum pump connected to the filter assembly, a sampling probe connected to the exhaust gas stream, an air distribution tube having a plurality of holes, a collar defining a first chamber about the air distribution tube, and a porous center tube having a plurality of micron-sized pores opening on an internal passage connected between the sampling probe and the filter assembly and defining a second chamber thereabout.

The dilution tunnel of the present invention has been found to substantially eliminate thermophoretic deposition of exhaust gas particulates on the internal walls thereof, and has an economical and particularly compact construction. An embodiment thereof controls the dilution ratio as a function of the transient operating conditions of the engine being tested.

BRIEF DESCRIPTION OF THE DRAWINGS

FIG. 1 is a diagrammatic cross sectional view of the gas sampling device of the present invention; and FIG. 2 is a view similar to FIG. 1 showing an alternate embodiment gas sampling device of the present invention.

BEST MODE FOR CARRYING OUT THE INVENTION

As is shown in FIG. 1, a gas sampling device 10 constructed in accordance with the present invention includes an improved dilution tunnel 12 having an air distribution tube 14 and a central axis 16. The air distribution tube 14 is preferably an elongate cylindrical tube of stainless steel or the like that has a plurality of distribution holes 18 radially therethrough in a central region 20 thereof, and opposite end portions 22 and 24 without such holes. In one embodiment, the tube 14 was 25.4 mm in outside diameter with a wall thickness of about 2.1 mm, and the holes were approximately 4 mm in diameter and arranged in six circumferential rows as shown. Each row had six holes spaced 60° apart, with the holes in adjacent rows being staggered or offset to promote more uniform flow distribution therethrough.

The dilution tunnel 12 also includes housing means 26 for forming an annular chamber 28 peripherally about the central region 20 of the air distribution tube 14. More particularly, housing means 26 includes an oval-shaped collar or barrel-shaped container 30 and an opposite pair of sealing rings 32 and 34 securely interconnecting the collar to the air distribution tube 14 intermediate the central region and the end portions 22 and 24. An inlet port 35 is formed radially through the collar 30 and is in communication with a controlled flow rate source of clean air, as is indicated generally by the reference number 36, under a relatively low pressure level, for example a pressure level of 55" of water (about 2 psi). In order to better regulate the flow rate of the diluent air into the chamber 28 the source 36 includes in serially arranged order a pressurized clean air reservoir 37, a manually adjustable pressure regulator 38, a critical flow restrictor or venturi 40 having a flow-controlling orifice 41 therein, and an air flowmeter 42. The pressure regulator 38 used was from C. A. Norgren Co. of Littleton, Colorado, and the air flowmeter used was from the American Meter Company of Philadelphia, Pennsylvania. Before reaching reservoir 37 the air in a pressurized supply line 43 is treated to improve its cleanliness, as by passing the air serially through a desiccant filter 44 to remove excess moisture and a charcoal scrubber 45 or the like to remove oil and/or hydrocarbons.

The dilution tunnel 12 further includes center tube means 46 for defining a second annular chamber 47 within the air distribution tube 14 along the central axis 16. Preferably, the center tube means 46 includes an elongate cylindrical porous center tube 48 of sintered stainless steel having a plurality of relatively small pores 50 opening inwardly into an internal passage 51. A porous tube having the desired precisely controlled porosity is commercially produced by Mott Metallurgical Corporation of Farmington, Connecticut. The center tube 48 used was 15.9 mm in outside diameter and had a wall thickness of about 1.6 mm. The individual pores 50 thereof were approximately 2 microns or less in size. The center tube means 46 also includes a pair of sealing rings 52 and 54 that are rigidly secured to the air distribution tube 14 and the center tube 48 at the opposite ends thereof.

The center tube 48 is connected to a sampling probe 56 by any conventional coupling, not shown, and typically extends within an engine exhaust pipe 58. The probe has a nose portion 60 defining an inlet passage 62 facing in an upstream direction. Thus, a proportionate sample of a particle-laden exhaust stream, as is indicated by the reference number 64, is directed to the interior of the inlet end of the porous center tube at the ring 52. The opposite or outlet end of the center tube 48, at the ring 54, is connected to a 90° ball valve 65 and a diagrammatically illustrated filter assembly 66 having an outer housing or in-line filter holder 67. The filter holder 67 is of the usual type such as is available from Geotech Environmental Equipment Inc. of Denver, Colorado. The filter assembly 66 also has a removable filter 68 as is schematically indicated, and such as those supplied by Pallflex, Inc. of Putnam, Connecticut. A filter of Teflon-impregnated fiber was used which had a diameter of 142 mm.

An outlet conduit 69 from the filter assembly 66 is in serial communication with a combined flowmeter 70 and a second critical flow restrictor or venturi 72 having an orifice 74. Both of the critical flow restrictors 40 and 70 are of conventional construction. A suction pump 76 having a capacity of 6 cubic feet per minute is serially connected to the output of the second critical flow restrictor 72. For example, a diaphragm vacuum type pump supplied by Thomas Industries Inc. of Louisville, Kentucky, has been found to be satisfactory.

Alternate Embodiment

The gas sampling device 10 of FIG. 1 is a relatively basic and low cost device for steady state measurements of the exhaust stream 64 which, unfortunately, requires extensive monitoring and a large number of mathematical calculations. In order to overcome these difficulties, an alternate embodiment gas sampling device 10' is illustrated in FIG. 2. In the alternate embodiment components similar to those described with respect to FIG. 1 will be described with identical reference numbers with a prime indicator affixed thereto.

One major distinction is the use of sophisticated mass flow controllers. Specifically, an electrically controlled, master mass flow controller (MFC2) 80 is used as a total flow rate controlling instrument, and an electrically controlled, slave mass flow controller (MFC1) 82 is used as an instrument for precisely controlling the diluent air flow rate from the reservoir 37'. These thermal mass flow controllers are preferably of the capillary tube-type commercially offered by Sierra Instruments of Carmel Valley, California, and operate substantially independently of normal temperature and pressure variations. The master controller 80 and slave controller 82 are respectively electrically connected to a microprocessor-based, ratio-establishing processor (PR) 84 by pairs of electrical lines 86,88 and 90,92 respectively.

Another major distinction is the use of an air flow rate meter (AM) 94, such as a venturi meter or Daniel flow meter, which measures the rate of incoming air supplied to an engine 95 to be sampled. The engine 95 is representatively shown in phantom box outline form for illustrative convenience. Also, a fuel flow rate meter (FM) 96 is provided to measure the rate of fuel being instantaneously supplied to the engine. The air flow rate meter 94 has a signal line 98 that is connected to a signal conditioner 100, and the fuel flow rate meter 96 has a signal line 102 connected also to the signal conditioner. The signal conditioner 100 preferably has two programmable electronic processing units therein, although not shown. One of these units is adaptable to convert the voltage signal in the signal line 98 by a first preprogrammed rate table to an electrical signal in a first outlet line 104 to the processor (PR) 84, and the other unit is adaptable to convert the frequency signal in the signal line 102 by a second preprogrammed rate table to an electrical signal in a second outlet line 106 to the processor.

Industrial Applicability

In the fixed proportion gas sampling device 10 of FIG. 1, the pressure regulator 38 and the ball valve 65 are opened immediately after the suction pump 76 is started to respectively communicate clean air reservoir 37 to the first chamber 28, and the passage 51 within the porous center tube 48 to the filter assembly 66. The orifice 41 of the critical flow restrictor 40 effectively limits the maximum flow rate of clean air to the flowmeter 42. Pressure readings P1 and P2 were taken upstream and downstream of the flowmeter 42 as is indicated in FIG. 1, and a first temperature reading T1 was taken at that flowmeter. Because mechanical flowmeters 42 and 70 were used, and they yield only uncorrected volume flow, it was necessary to convert the data into standard values and, subsequently mass flow, by taking such readings and manipulating the information. The pressure reading P2 was maintained at an equivalent of approximately 55 inches of water, or about 2 psi, to the first annular chamber 28. The diluent air was thereafter broadly distributed to the second annular chamber 47 by way of the distribution holes 18. Subsequently, the micropores 50 in the center tube 48 maintained uniform pressure levels across the axial length of the chamber 47 and evenly distributed diluent air in a plurality of streams into the passage 51. This advantageously provided a boundary layer film of relatively clean and cool air that insulated and protected the internal surface of the center tube 48 from direct contact by the exhaust stream 64 entering the sampling probe 56 from the exhaust pipe 58. Moreover, the Reynolds number within the center tube 48 was maintained above about 4,000 in order to insure a turbulent flow regime for adequate mixing of the diluent air and exhaust gas sample.

Pressure readings P3 and P4 were taken upstream and downstream of the filter assembly 66, and another pressure reading P5 was taken downstream of the combined flowmeter 70 as is indicated in FIG. 1. Furthermore, temperature readings T2 were taken of the body of the filter holder 67, T3 of the combined stream within the filter assembly 66, and T4 of the combined stream at the combined flowmeter 70. Temperatures T1 and T4 respectively reflect the air and mixed flow conditions existing in the critical flow restrictors 40 and 72, and may be used to confirm the flow rates through the orifices 41 and 74.

In operation, the flowmeters 42 and 70, and the critical flow restrictors 40 and 72 were very successful in maintaining a air-to-gas dilution ratio of approximately 10:1 even though the ambient air temperature and exhaust stream temperature varied over a substantial range. The capacity of the suction pump 74 was effective in positively and continuously drawing a critical vacuum across the orifice 74 of the second critical flow restrictor 72. In other words, the filtered air and exhaust stream mixture reached sonic speed in the orifice 74, and this is the maximum velocity that can occur therethrough. Accordingly, such combination inherently provides a constant flow device. The first critical flow restrictor 40 operates in the same manner. In one instance the critical flow rates through the orifices 41 and 74 were 90 and 98 liters per minute respectively. It is to be appreciated that the pressure regulator 38 could be manually adjusted between tests to modify the pressure level of the diluent air at the entrance of the critical flow restrictor 40. This can allow the dilution ratio to be modified within a preselected range by effecting the air mass flow rate permitted by the critical flow restrictor 40.

In one embodiment of FIG. 1 the overall length of the dilution tunnel 12, from the ring 52 to the ring 54, was only 14 inches at a maximum diameter of about 2½ inches. The entire sampling system 10 resided on a lab cart of 30×36 inches with three shelves. Further reductions are probable with the replacement of the relatively bulky mechanical totalizing flowmeters 42 and 70. Furthermore, the undiluted length of the sampling probe 56 should be kept to a minimum in order to minimize particle deposition on the walls of the inlet passage 62 prior to reaching the porous center tube 48. For example, the distance between the porous center tube and the exhaust pipe 58 should be maintained below one foot or one third of a meter.

The second embodiment sampling device 10' of FIG. 2 eliminates the need for the critical flow restrictors 40 and 72 and the mechanical type flow totalizing meters 42 and 70 of FIG. 1. This is accomplished by the use of the capillary tube-type thermal mass flow controllers 80 and 82 electrically driven by the microprocessor-based ratio-establishing processor 84. The processor 84 receives electrical input from the signal conditioner 100 reflecting the instantaneous total inlet air flow rate information and the total inlet fuel flow rate information to the engine 95 as supplied by the meters 94 and 96 respectively. In this manner a proportional raw exhaust gas sampling device 10' is provided that is capable of reacting to transient engine conditions while substantially eliminating particle deposition and entrainment. For example, the ratio-establishing processor 84 can apportion the control signals in the lines 86 and 88 to the master mass flow controller 80, and the control signals in the lines 90 and 92 to the lesser flow capacity slave mass flow controller 82 to establish an approximate ratio of flow of about 1.1 to 1.0, yielding a typical dilution ratio of about 10:1. This value should be controllable and variable.

The dilution tunnel 12 has been proven to virtually eliminate particle deposition by thermophoresis or other means. Additionally, its small physical size satisfies the stated criterion for portability. In marked contrast to the systems disclosed in U.S. Pat. Nos. 4,586,367 and 4,660,408 wherein flow concerns are centered around the control of secondary dilution air for the appropriate temperature reduction of a constant volume sample stream versus the total filtered sample flow, the invention disclosed in FIG. 2 addresses proportional raw (undilute) sampling with respect to total engine transient exhaust flow and establishes a means for subsequent control of cooling dilution air with a master-slave pair of mass flow controllers 80 and 82.

Other aspects, objects and advantages of this invention can be obtained from a study of the drawings, the disclosure, and the appended claims.

What is claimed is:

1. A dilution tunnel adapted for use in a gas sampling device including a sampling probe disposed in an exhaust gas stream, a source of clean and pressurized diluent air, and a filter assembly, comprising:
    an air distribution tube having a plurality of distribution holes therethrough;
    housing means for forming a first chamber peripherally about the air distribution tube, the chamber being connectable to the clean air source; and
    center tube means for defining a second chamber within the air distribution tube, the center tube means including a porous center tube having a plurality of micron-sized pores and an internal passage serially connected between the sampling probe and the filter assembly.

2. The dilution tunnel of claim 1 as adapted for use in a gas sampling device having a critical flow restrictor downstream of the filter assembly and suction pump means for drawing a critical vacuum across the critical flow restrictor and providing a relatively constant total flow rate therethrough.

3. The dilution tunnel of claim 2 wherein the clean air source includes a pressurized reservoir and another critical flow restrictor located serially between the pressurized reservoir and the first chamber.

4. The dilution tunnel of claim 3 wherein the clean air source includes an adjustable pressure regulator between the pressurized reservoir and the another critical flow restrictor for varying the dilution ratio.

5. The dilution tunnel of claim 1 wherein, in use, within the center tube the Reynolds number is above about 4,000 and turbulent flow exists in the internal passage 51 of the porous center tube.

6. A gas sampling device for measuring the amount of particulates in an exhaust gas stream comprising:
    diluent air source means for supplying clean air under pressure;
    an air distribution tube having a plurality of holes therethrough;
    a collar defining a first chamber about the air distribution tube that is connected to the air source means;
    a porous center tube having a plurality of micron-sized pores therethrough in communication with an internal passage and defining a second chamber thereabout and within the air distribution tube;
    a sampling probe adapted to connect the exhaust gas stream to the internal passage of the porous center tube;
    a filter assembly connected to the internal passage of the porous center tube; and
    a vacuum pump connected to the filter assembly.

7. The gas sampling device of claim 6 including a first mass flow controller located serially between the air source means and the first chamber, a second mass flow controller located serially between the filter assembly and the vacuum pump, and control means for electrically controlling the mass flow controllers and respectively adjusting the rate proportion of diluent air and of the mixture of diluent air and a sample of the exhaust stream.

8. The gas sampling device of claim 7 wherein the control means includes a microprocessor-based, ratio-establishing processor electrically connected to both of the mass flow controllers.

9. The gas sampling device of claim 8 wherein the control means includes an air flow rate meter adapted to measure the total flow rate of intake air to the engine, a fuel flow rate meter adapted to measure the total rate of fuel supplied to the engine, and a signal conditioner electrically connected to the ratio-establishing processor and to both the air flow rate meter and the fuel flow rate meter.

10. The gas sampling device of claim 6 wherein, in use, within the center tube the Reynolds number is above about 4,000 and turbulent flow exists in the internal passage of the porous center tube.

* * * * *